(12) United States Patent
Wang et al.

(10) Patent No.: US 9,587,976 B2
(45) Date of Patent: Mar. 7, 2017

(54) PHOTOACOUSTIC PROBE (75) Inventors: Xingwei Vivian Wang, Shrewsbury, MA (US); Nan Wu, Lowell, MA (US)

(73) Assignee: UNIVERSITY OF MASSACHUSETTS, Boston, MA (US)

(*) Notice: Subject to any disclaimer, the term of this patent is extended or adjusted under 35 U.S.C. 154(b) by 575 days.

(21) Appl. No.: 13/984,736

(22) PCT Filed: Feb. 17, 2012

(86) PCT No.: PCT/US2012/025646
§ 371 (c)(1),
(2), (4) Date: Aug. 9, 2013

(87) PCT Pub. No.: WO2012/112890
PCT Pub. Date: Aug. 23, 2012

(65) Prior Publication Data
US 2013/0319123 A1   Dec. 5, 2013

Related U.S. Application Data

(60) Provisional application No. 61/443,925, filed on Feb. 17, 2011.

(51) Int. Cl.
*G01N 29/24* (2006.01)
*G01H 9/00* (2006.01)
(Continued)

(52) U.S. Cl.
CPC .......... *G01H 9/004* (2013.01); *A61B 5/0084* (2013.01); *A61B 5/0095* (2013.01);
(Continued)

(58) Field of Classification Search
CPC .......... G01H 9/004; G01H 9/006; A61B 8/08; A61B 8/12; A61B 2562/12; A61B 5/0095; G01N 29/2418
(Continued)

(56) References Cited

U.S. PATENT DOCUMENTS 3,532,181 A  10/1970 DeMaria et al.
4,329,058 A   5/1982 James et al.
(Continued)

FOREIGN PATENT DOCUMENTS

EP   0 389071 B   1/1990
EP   1 078 227 B1  7/2002
(Continued)

OTHER PUBLICATIONS

Notification of the International Search Report and the Written Opinion for Int'l Application No. PCT/US2012/025646; entitled: Photoacoustic Probe; Date Mailed: Jan. 2, 2013.
(Continued)

*Primary Examiner* — Laura Martin
*Assistant Examiner* — Rose M Miller
(74) *Attorney, Agent, or Firm* — Hamilton, Brook, Smith & Reynolds, P.C.

(57) ABSTRACT

A photoacoustic transducer, such as a photoacoustic probe includes an optical fiber, diaphragm, at the optical fiber, whereby the optical fiber and diaphragm define a cavity, and an energy absorption film at the optical fiber, whereby an activating laser directed through the optical fiber can excite the energy absorption film to thereby generate an acoustic wave that, upon reflection upon a remote surface, can deflect the diaphragm and modify reflection of a detecting laser also directed through the optical fiber. A method of detecting an acoustic wave includes directing an activating laser through an optical fiber to an energy absorption film at the optical fiber, directing a detecting laser through the optical fiber and cavity to the diaphragm at the optical fiber, and measuring an interference pattern generated at least in part by reflection of the detecting laser from a surface of the diaphragm.

42 Claims, 5 Drawing Sheets

(51) Int. Cl.
*A61B 5/00* (2006.01)
*A61B 8/12* (2006.01)
*A61B 8/08* (2006.01)

(52) U.S. Cl.
CPC ............ *G01N 29/2418* (2013.01); *A61B 8/08* (2013.01); *A61B 8/12* (2013.01); *A61B 2562/12* (2013.01)

(58) Field of Classification Search
USPC .......................................... 73/655, 657, 643
See application file for complete search history.

(56) References Cited

U.S. PATENT DOCUMENTS

| | | | |
|---|---|---|---|
| 4,503,564 A * | 3/1985 | Edelman | H04R 23/008 381/164 |
| 4,639,091 A | 1/1987 | Huignard et al. | |
| 4,652,744 A | 3/1987 | Bowers et al. | |
| 4,678,904 A | 7/1987 | Saaski et al. | |
| 4,682,500 A | 7/1987 | Uda | |
| 4,942,767 A | 7/1990 | Haritonidis et al. | |
| 5,087,124 A | 2/1992 | Smith et al. | |
| 5,101,664 A | 4/1992 | Hockaday et al. | |
| 5,247,490 A | 9/1993 | Goepel et al. | |
| 5,301,001 A | 4/1994 | Murphy et al. | |
| 5,324,282 A | 6/1994 | Dodick | |
| 5,365,789 A | 11/1994 | Totterdell et al. | |
| 5,381,231 A | 1/1995 | Tu | |
| 5,392,117 A | 2/1995 | Belleville et al. | |
| 5,528,367 A | 6/1996 | Putnam et al. | |
| 5,559,358 A | 9/1996 | Burns et al. | |
| 5,615,675 A | 4/1997 | O'Donnell et al. | |
| 5,747,705 A | 5/1998 | Herb et al. | |
| 5,891,747 A | 4/1999 | Farah | |
| 5,920,521 A | 7/1999 | Kromer et al. | |
| 5,944,687 A | 8/1999 | Benett et al. | |
| 6,066,098 A | 5/2000 | Masotti et al. | |
| 6,281,976 B1 | 8/2001 | Taylor et al. | |
| 6,304,686 B1 | 10/2001 | Yamate et al. | |
| 6,309,352 B1 | 10/2001 | Oraevsky et al. | |
| 6,322,557 B1 | 11/2001 | Nikolaevich et al. | |
| 6,328,482 B1 | 12/2001 | Jian | |
| 6,405,069 B1 | 6/2002 | Oraevsky et al. | |
| 6,513,390 B1 | 2/2003 | De La Puente et al. | |
| 6,519,376 B2 | 2/2003 | Biagi et al. | |
| 6,527,455 B2 | 3/2003 | Jian | |
| 6,567,173 B1 | 5/2003 | Johannesen | |
| 6,738,145 B2 | 5/2004 | Sherrer et al. | |
| 6,820,487 B2 | 11/2004 | Esashi et al. | |
| 6,925,213 B2 | 8/2005 | Boyd et al. | |
| 6,933,490 B1 | 8/2005 | Vidovic et al. | |
| 6,934,015 B1 | 8/2005 | Vidovic et al. | |
| 7,054,011 B2 | 5/2006 | Zhu et al. | |
| 7,060,965 B2 | 6/2006 | Vidovic et al. | |
| 7,149,374 B2 | 12/2006 | Lagakos et al. | |
| 2002/0159671 A1 | 10/2002 | Boyd et al. | |
| 2003/0138185 A1 | 7/2003 | Dianov et al. | |
| 2004/0047536 A1 | 3/2004 | Pickerell et al. | |
| 2004/0067000 A1 | 4/2004 | Bates et al. | |
| 2004/0071383 A1 | 4/2004 | Balachandran et al. | |
| 2004/0077949 A1 | 4/2004 | Blofgett et al. | |
| 2004/0086228 A1 | 5/2004 | Rumpf et al. | |
| 2005/0041905 A1 | 2/2005 | Lagakos et al. | |
| 2005/0157305 A1 | 7/2005 | Yu et al. | |
| 2005/0195402 A1 | 9/2005 | May et al. | |
| 2005/0195403 A1 | 9/2005 | Xu et al. | |
| 2005/0231729 A1 | 10/2005 | Lopushansky et al. | |
| 2005/0243308 A1 | 11/2005 | Vidovic et al. | |
| 2006/0126991 A1 | 6/2006 | Huang | |
| 2007/0006663 A1 | 1/2007 | Zerwekh et al. | |
| 2007/0147738 A1 | 6/2007 | Wang et al. | |
| 2008/0159687 A1 | 7/2008 | Donlagic et al. | |
| 2009/0202195 A1 | 8/2009 | Lagakos et al. | |
| 2009/0226128 A1 | 9/2009 | Donlagic et al. | |
| 2009/0259150 A1 | 10/2009 | Ostrovsky et al. | |
| 2009/0279099 A1 | 11/2009 | Wang et al. | |
| 2009/0289198 A1 | 11/2009 | Youngner | |
| 2009/0320605 A1 | 12/2009 | Antila et al. | |
| 2010/0007893 A1 | 1/2010 | Hall | |
| 2010/0058871 A1 * | 3/2010 | Takeishi | G01N 29/2418 73/627 |
| 2010/0135111 A1 | 6/2010 | Bates et al. | |
| 2010/0179432 A1 | 7/2010 | Thornton | |
| 2010/0206082 A1 * | 8/2010 | Shimazaki | G01N 29/043 73/627 |
| 2011/0048136 A1 | 3/2011 | Birch et al. | |
| 2012/0116255 A1 | 5/2012 | Wang et al. | |
| 2013/0319123 A1 | 12/2013 | Wang et al. | |
| 2014/0180056 A1 * | 6/2014 | Hoseit | A61B 5/6851 600/407 |
| 2014/0208858 A1 | 7/2014 | Jiang et al. | |
| 2014/0270623 A1 | 9/2014 | Ahmed et al. | |
| 2015/0141854 A1 | 5/2015 | Eberle et al. | |

FOREIGN PATENT DOCUMENTS

| | | |
|---|---|---|
| JP | 61191932 A | 8/1986 |
| WO | WO 94/02810 | 2/1994 |
| WO | WO 99/60341 | 11/1999 |
| WO | WO 02/23148 | 3/2002 |
| WO | WO 2005/024339 A2 | 3/2005 |
| WO | WO 2007/019676 A1 | 2/2007 |
| WO | WO 2008/092372 A1 | 8/2008 |
| WO | WO 2011/008559 A1 | 1/2011 |

OTHER PUBLICATIONS

Aarabi, P., "Self-localizing dynamic microphone arrays," *IEEE Transactions on Systems, Man and Cybernetics—Part C: Applications and Reviews*, 32(4): 474-484 (2002).

Acquafresca, A., et al., "Toward Virtual Biopsy Through an All Fiber Optic Ultrasonic Miniaturized Transducer: A Proposal," IEEE Transactions on Ultrasonics, Ferroelectrics and Frequency Control, 50(10): 1325-1335 (2003).

Acquafresca, A., et al., "Fiber Optics Sensors for Ultrasonic Virtual Biopsy," Proceedings of IEEE Sensors, 1: 261-265 (2002).

Alberts, C. J., et al., "Fiber-Top Refractometer," Measurement Science and Technology, 20(3): 034005 (2009).

Andreev, V. G., et al., "Optoacoustic tomography of breast cancer with arc-array Transducer," Biomedical Optoacoustics, San Jose, CA, USA, 3916, pp. 36-47 (2000).

Aris, T., et al., "Optical beam steering using a liquid-crystal television panel", Microwave and Optical Technology Letters, 7(6): 285-289 (1994).

Balageas, D. L., et al., "Ultrasound generation in composites via embedded optical fiber," in Review of Progress in Quantitative Nondestructive Evaluation, D. Thompson and D. Chimenti, eds., AIP Conf., pp. 691-698 (1998).

Beard, P. C., et al., "Optical fiber photoacoustic-photothermal probe," 23: 1235-1237 (1998).

Beard, P.C., et al., "Characterization of Post-Mortem Arterial Tissue Using Time Resolved Photoacoustic Spectroscopy at 436, 461 and 532nm," Physics in Medicine and Biology, 42: 177-198 (1997).

Beard, P.C., et al., "Comparison of a Miniature Ultrasonic Optical Fibre Hydrophone With PVDF Hydrophone Technology," in Proceedings IEEE International Ultrasonics Symposium, pp. 1881-1883 (1998).

Biagi, E., et al., "Generatore optoacustico di ultrasuoni da energia laser alimentata tramite fibra ottica", Italian, FI 2000 A 000176, International Extension Requested (2000).

Biagi, E., et al., "Photoacoustic Generation: All-Optical Fibre Transducers," in Proceedings IEEE International Ultrasonics Symposium, pp. 921-924 (1996).

Biagi, E., et al., "Photoacoustic Generation: Optical Fiber Ultrasonic Sources for Non-Destructive Evaluation and Clinical Diagnosis," Optical Review, 4(4): 481-483 (1997).

Biagi, E., et al., "All optical fiber ultrasonic sources for non destructive testing and clinical Diagnosis," Optical Sensors and Microsystems (2000).

(56) References Cited

OTHER PUBLICATIONS

Biagi, E., et al., "Efficient laser-ultrasound generation by using heavily absorbing films as Targets," IEEE Transactions on Ultrasonics, Ferroelectrics and Frequency Control, 48(6): 1669-1680 (2001).
Biagi, E., et al., "Fiber optic broadband ultrasonic probe," IEEE Sensors Conference, pp. 363-366 (2008).
Biagi, E., et al., "Fiber optic photoacoustic device: high efficiency and wide bandwidth ultrasonic source", IEEE Conference Proceedings, Instrumentation and Measurement Technology Conference, pp. 948-952, 1998.
Biagi, E., et al., "Guided acoustic wave propagation for porcelain coating Characterization," IEEE Transactions on Ultrasonics, Ferroelectrics and Frequency Control, 44(4): 909-916 (1997).
Biagi., E., et al., "Real Time Processing of the Radiofrequency Echo Signal for On-Line Spectral Maps," Acoustic Imaging, vol. 24: pp. 95-100 (2000).
Bobbin, "(EMAT)—High-Temperature Probe Electromagnetic Acoustic Transducer," Materials Evaluation, 37 (5): pp. 28 (1979).
Bonello, B., et al., "Application of the Picosecond Ultrasonic Technique to the Study of Elastic and Time-Resolved Thermal Properties of Materials," Ultrasonics, 35(3): 223-231 (1997).
Boonsang, S., and Dewhurst, R. J., "Signal Enhancement in Rayleigh Wave Interactions Using a Laser-Ultrasound/EMAT Imaging System," Ultrasonics, 43(7): 512-523 (2005).
Bost, W., et al., "Developing a high-resolution photoacoustic microscopy platform," 4th European Conference of the International Federation for Medical and Biological Engineering, pp. 448-451 (2009).
Bowen, T., "Radiation-Induced Thermoacoustic Soft Tissue Imaging," in Proceedings IEEE International Ultrasonics Symposium, pp. 817-822 (1981).
Bretz, K. C., et al., "Picosecond Acoustics for the Characterization of Sub-Micron Polymeric Films," Ultrasonics, 34(2-5): 513-515 (1996).
Buffat, P., and Borel, J.-P., "Size effect on the melting temperature of gold particles," Physical Review A, 13(6): 2287-2298 (1976).
Buma, T., et al., "High-frequency ultrasound array element using thermoelastic expansion in an elastomeric film," Applied Physics Letters, 79(4): 548-550 (2001).
Buma, T., et al., "Thermoelastic Expansion vs. Piezoelectricity for High-Frequency, 2-D Arrays," IEEE Transactions on Ultrasonics, Ferroelectrics and Frequency Control, 50 (8): 1065-1068 (2003).
Calasso, I. G., et al., "Photoacoustic point source," Physical Review Letters, 86: 3550-3553 (2001).
Caller, R.F., et al., "Laser Ultrasound for Investigation of Arteriosclerotic Arterial Tissue," IEEE Colloquium Digest, vol. 97/124, pp. 4/1-4/6 (1997).
Carmena, J. M., et al., "The Use of Doppler in Sonar-Based Mobile Robot Navigation: Inspirations From Biology," Information Sciences, 161(1-2): 71-94 (2004).
Cassarly, W. J., et al., "Phase control of coherent diode laser arrays using liquid crystals," Proceedings SPIE, Laser Diode Technology and Applications, Luis Figueroa, Ed, pp. 130 (1989).
Cha, N.-G., et al., "Convective Assembly and Dry Transfer of Nanoparticles Using Hydrophobic/Hydrophilic Monolayer Templates," Langmuir, 25(19): 11375-11382 (2009).
Chen, Q. X., et al., "A new laser-ultrasound transducer for medical applications," Ultrasonics, 32: 309-313 (1994).
Cheng, A., et al., "Simulation of laser-generated ultrasonic waves in layered plates," Journal of the Acoustical Society of America, 110(2): 848-855 (2001).
Chiota, J., et al., "Multiscale Directed Assembly of Polymer Blends Using Chemically Functionalized Nanoscale-Patterned Templates," Small, 5(24): pp. 2788-2791 (2009).
Chu, E., et al., "Intracardiac echocardiography during radiofrequency catheter ablation of cardiac arrhythmias in humans," Journal of the American College of Cardiology, 24: 1351-1357 (1994).

Cibula, E., and Donlagic, D., "Miniature fiber-optic pressure sensor with a polymer Diaphragm," Applied optics, 44(14): pp. 2736-2744 (2005).
Coleman, A.J., et al., "Acoustic Performance and Clinical Use of a Fibreoptic Hydrophone,", Ultrasound in Medicine and Biology, 24(1): 143-151 (1998).
Connor, E.E., et al., "Gold nanoparticles are taken up by human cells but do not cause acute cytotoxicity," Small, 1(3): 325-327 (Mar. 2005).
Coulette, R., et al., "Laser-generated ultrasound applied to two-layered materials characterization: Semi-analytical model and experimental validation," Ultrasonics, 36: 239-243 (1998).
Crazzolara, H, et al., "Analysis of the Acoustic Response of Vascular Tissue Irradiated by an Ultraviolet Laser Pulse," Journal of Applied Physics, 70(3): 1847-1849 (1991).
Cross, F.W., et al., "Ablative and Acoustic Response of Pulsed UV Laser-Irradiated Vascular Tissue in a Liquid Environment," Journal of Applied Physics, 64(4): 2194-2201 (1988).
Davies, J. P., "Surface-enhanced Raman scattering from sputter-deposited silver surfaces," Analytical Chemistry, 58: 1290-1294, (1986).
Davies, S. J., et al., "Laser-generated ultrasound: its properties, mechanisms and multifarious applications," Journal of Physics D: Applied Physics, 26(3): 329 (1993).
Dubois, M., et al., "Modeling of laser thermoelastic generation of ultrasound in an orthotropic medium," Applied Physics Letters, 64(5): 554-556 (1994).
Dutton, B., et al., "A New Magnetic Configuration for a Small In-Plane Electromagnetic Acoustic Transducer Applied to Laser-Ultrasound Measurements: Modelling and Validation," Sensors and Actuators A: Physical, 125(2): 249-259 (2006).
Dutton, B., et al., "Modeling of Magnetic Fields to Enhance the Performance of an In-plane EMAT for Laser-Generated Ultrasound," Ultrasonics, 44(Supplement 1): e657-e665 (2006).
Ebbini, E. S., and Cain, C. A., "Multiple-focus ultrasound phased-array pattern synthesis: optimal driving-signal distributions for hyperthermia," IEEE Transactions on Ultrasonics, Ferroelectrics and Frequency Control, 36(5): 540-548 (1989).
El-Sayed, M. A., "Some interesting properties of metals confined in time and nanometer space of different shapes," Accounts of Chemical Research, 34(4): 257-264 (2001).
Enüstün, B. V., and Turkevich, J., "Coagulation of Colloidal Gold," Journal of the American Chemical Society, 85(21): 3317-3328 (1963).
Epstein, L.M., et al., "Nonfluoroscopic transseptal catheterization: safety and efficacy of intracardiac echocardiographic guidance," Journal of Cardiovascular Electrophysiology, 9: 625-630 (1998).
Esenaliev, R. O., et al., "Studies of acoustical and shock waves in the pulsed laser ablation of biotissue," Lasers in Surgery and Medicine, 13(4): 470-484 (1993).
Eustis, S., et al., "Why Gold Nanoparticles Are More Precious Than Pretty Gold: Noble Metal Surface PlasmonResonance and Its Enhancement of the Radiative and Nonradiative Poperties of Nanocrystals of Different Shapes," Chemcial Society Reviews, 35(3): 209-217 (2006).
Fan, G., and Zhiyong G., "Nano-soldering of magnetically aligned three-dimensional nanowire networks," Nanotechnology, 21(11): 115604 (2010).
Fang, Q., et al., "Effect of optical penetration on laser generated thermoelastic ultrasound in solids," Acta Acustica, 21: 165-173 (1996).
Fatemi, M., and Greenleaf, J. F., "Vibro-acoustography: An imaging modality based on ultrasound-stimulated acoustic emission," Proceedings of the National Academy of Sciences of the United States of America, pp. 6603-6608 (1999).
Federspila, Ph. A., et al., "Ultrasound-Based Navigation of Robotic Drilling at the Lateral Skull Base," InternationalCongress Series, vol. 1256: pp. 1358-1358 (2003).
Fisher, W. G., et al., "Adjunctive intracardiac echocardiography to guide slow pathway ablation in human atrioventricular nodal reentrant tachycardia: anatomic insights," Circulation, 96: 3021-3029 (1997).

(56) References Cited

OTHER PUBLICATIONS

Fleischman, A., et al., "Miniature High Frequency Focused Ultrasonic Transducers for Minimally Invasive Imaging Procedures," Sensors and Actuators A: Physical, 103(1-2): 76-82 (2003).
Fomitchov, P. A., et al., "Photoacoustic probes for nondestructive testing and biomedical Applications," Applied Optics, 41(22): 4451-4459 (2002).
Fomitchov, P. A., et al., "Distributed photoacoustic system for cure monitoring of Composites," Advanced Nondestructive Evaluation for Structural and Biological Health Monitoring, Newport Beach, CA, USA, 4335, pp. 323-329 (2001).
Fomitchov, P. A., et al., "Fiberized laser ultrasonic source for process monitoring and biomedical applications," Applications of Optical Fiber Sensors, Glasgow, United Kingdom, 4074, pp. 127-134 (2000).
Fomitchov, P. A., et al., "Laser ultrasonic enabled "Smart" mold for composite parts Manufacturing," Review of Progress in Quantitative Nondestructive Evaluation, Ames, Iowa, pp. 802-1807 (2001).
Foster, F.S., "Transducer Materials and Probe Construction," Ultrasound in Medicine and Biology, 26: S2-S5 (2000).
Gao, F., et al., "Synthesis, Characterization, and Thermal Properties of Nanoscale Lead-Free Solders on Multisegmented Metal Nanowires," The Journal of Physical Chemistry C, 113(22): 9546-9552 (2009).
Ge, J., et al., "Intravascular Ultrasound Imaging of Angiographically Normal Coronary Arteries: A Prospective Study In Vivo," British Heart Journal, 71(6): 572-578 (1994).
Gibbons, M.T., "Engineering by the Numbers," http://www.asee.org/publications/profiles/upload/2008ProfileEng.pdf.
Goltsos, W., and Holz, M., "Agile beam steering using binary optics microlens arrays," Optical Engineering, 11(29): 1392-1397 (1990).
Grahn, H.T., et al., "Picosecond Ultrasonics," Journal of Quantum Electronics, 25(12): 2562-2569 (1989).
Green, D. E., et al., "The Effect of Nanoparticle-Enhanced Photoacoustic Stimulation on Multipotent Marrow Stromal Cells," ACS Nano, 3(8): 2065-2072 (2009).
Guittet, C. et al., "High-Frequency Estimation of the Ultrasonic Attenuation Coefficient Slope Obtained in Human Skin: Simulation and In Vivo Results," Ultrasound in Medicine and Biology, 25(3): 421-429 (1999).
Guthy, C.J., et al., "A Review of Temperature Measurement Methods During Twist Drilling Processes," Journal of Manufacturing Processes, (Submitted).
Haga, Y., et al., "Batch Fabrication of Intravascular Forward-Looking Ultrasonic Probe," Sensors and Actuators A: Physical,104(1): 40-43 (2003).
Handzel, A. A., and Krishnaprasad, P. S., "Biomimetic sound-source localization," IEEE Sensors Journal, 2(6): 607-616 (2002).
He, J. A., et al., "Electrostatic multilayer deposition of a gold-dendrimer nanocomposite," Chemistry of Materials, 11: 3268-3274 (1999).
http://www.enme.umd.edu/news/news_story.php?id=2612 (Miao Yu Receives AFOSR YIP Award) (retrieved from internet Aug. 22, 2014).
http://www.olympus-ims.com/en/probes (retrieved from internet Aug. 22, 2014).
http://www.ptca.org/ivus/ivus.html (Angioplasty.org, "IVUS Overview") (retrieved from internet Aug. 22, 2014).
http://www.ptca.org/news/2007/0530.html (Angioplasty.org, IVUS News, "Most Heart Stents Are Placed Imperfectly, Increasing Risk of Heart Attack or Reclosure") (retrieved from internet Aug. 22, 2014).
http://www.redwoodeditor.com/content/SCAI/scai/ (On 30th Anniversary, Angioplasty Celebrated as Modern Medical Breakthrough in Stopping Heart Attack) (retrieved from internet Aug. 22, 2014).
Hua, F., et al., "Patterning of Layer-by-Layer Self-Assembled Multiple Types of Nanoparticle Thin Films by Lithographic Technique," Nano Letters, 2(11): 1219-1222 (2002).
Long, M., et al., "Simulation of the Path Loss for Radio Wave Propagation Based on MATLAB Language," Acta Scientiarum Naturalium UniversitatisSunyatseni, 40: 18-20 (2001).
Huang, X., et al., "Cancer cell imaging and photothermal therapy in the near-infrared region by using gold nanorods." Journal of the American Chemical Society, 128(6): 2115-2120 (2006).
Huber, F., et al., "Analyzing Refractive Index Changes and Differential Bending in Microcantilever Arrays," Review of Scientific Instruments, 79(8): 086110-3 (2008).
Huber, F., et al., "Label Free Analysis of Transcription Factors Using Microcantilever Arrays", Biosensors and Bioelectronics, 21(8):, pp. 1599-1605 (2006).
Huber, T. M., "Noncontact modal testing of hard-drive suspensions using ultrasound radiation force", Proceedings of International Modal Analysis Conference (IMAC XXIV), 2006.
Huber, T. M., et al., "Noncontact Modal Analysis of a Pipe Organ Reed Using Airborne Ultrasound Stimulated Vibrometry," Journal of the Acoustical Society of America, 119(4): 2476-2482 (2006).
Huber, T. M., et al., "Non-Contact Mode Excitation of Small Structures in Air Using Ultrasound Radiation Force," Journal of the Acoustical Society of America, 117(4): 2455-2455 (2005).
Huber, T.M., et al., "Mode-selective noncontact excitation of microcantilevers and microcantilever arrays in air using the ultrasound radiation force," Applied Physics Letters, 97:214101(2010).
Huber, T.M., et al., "Excitation of Vibrational Eigenstates of Coupled Microcantilevers Using Ultrasound Radiation Force," Proceedings of the ASME 2008 International Design Engineering Technical Conferences& Computers and Information in Engineering Conference IDETC/CIE, Brooklyn, New York, USA (2008).
Hyde, J.S., and Mertz, I.E., "Gender, Culture, and Mathematics Performance," Proceedings of the National Academy of Sciences of the United States of America, pp. 8801-8807 (2009).
Iannuzzi, D., et al., "A Fiber-Top Cantilever for Hydrogen Detection," Sensors and Actuators B: Chemical, 121 (2): 706-708 (2007).
Iannuzzi, D., et al., "Fiber-Top Atomic Force Microscope," Review of Scientific Instruments, 77(10): 106105-3 (2006).
Iannuzzi, D., et al., "Monolithic Fiber-Top Sensor for Critical Environments and Standard Applications," Applied Physics Letters, 88(5): 053501 (2006).
Jackson, S., "The Quiet Crisis: Falling Short in Producing American Scientific and Technical Talent," Building Engineering and Science Talent (2002).
Jain, P. K., et al., "Calculated Absorption and Scattering Properties of Gold Nanoparticles of Different Size, Shape, and Composition: Applications in Biological Imaging and Biomedicine," The Journal of Physical Chemistry B, 110(14): 7238-7248 (2006).
Kalman, J. M., et al., "Activation and entrainment mapping defines the tricuspid annulus as the anterior barrier in typical atrial flutter," Circulation, 94: 398-406 (1996).
Kalman, J. M., et al., "In vitro quantification of radiofrequency ablation lesion size using intracardiac echocardiography in dogs," American Journal of Cardiology, 77: 217-219 (1996).
Kalman, J. M., et al., "Radiofrequency catheter modification of sinus pacemaker function guided by intracardiac echocardiography," Circulation, pp. 3070-3081 (1995).
Kalman, J. M., et al., ""Cristal tachycardias": origin of right atrial tachycardias from the crista terminalis identified by intracardiac echocardiography," Journal of the American College of Cardiology, 31: 451-459 (1998).
Kapralos, B., et al., "Audio-visual localization of multiple speakers in a video teleconferencing setting," International Journal of Imaging Systems and Technology, Special Issue on Facial Image Processing, Analysis and Synthesis, 13(1): 95-105 (2003).
Karabutov, A. A., et al., "Backward mode detection of laser-induced wideband ultrasonic transients with optoacoustic transducer," Journal of Applied Physics, 87: 2003-2014 (2000).
Kim, J.-W., et al., "Golden carbon nanotubes as multimodal photoacoustic and photothermal high-contrast molecular agents," Nat Nano, 4(10): 688-694 (2009).
Knight J., and Degertekin, L., "Capacitive Ultrasonic Transducers for Forward Looking Intravascular Imaging Arrays," In Proceedings IEEE International Ultrasonics Symposium, pp. 1052-1055 (2002).

(56) References Cited

OTHER PUBLICATIONS

Kopchok, G. E., et al., "Principles and Devices," Seminars in Vascular Surgery, 19(3): 128-131 (2006).

Kruger, R. A., and Liu, P., "Photoacoustic ultrasound: Pulse production and detection in 0.5% Liposyn," Medical Physics, 21(7): 1179-1184 (1994).

Lanza di Scalea, F., et al., "Remote laser generation of narrow-band surface waves through optical fibers," IEEE Transactions on Ultrasonics, Ferroelectrics and Frequency Control, 46: 1551-1557 (1999).

Li, C., and Wang, L. V., "Photoacoustic tomography and sensing in biomedicine," Physics in Medicine and Biology, 54(19): R59 (2009).

Li, P., et al., "Photoacoustic flow measurements by use of laser-induced shape transitions of gold nanorods," Optics Letters,30(24): 3341-3343 (2005).

Li, X., et al., "Fabrication and Integration of Metal Oxide Nanowire Sensors Using Dielectrophoretic Assembly and Enhanced Post-assembly Processing," Sensors and Actuators B, 148: 404-412 (2010).

Lifante, G., [Integrated Photonics: fundamentals], John Wiley & Sons Ltd., England; pp. 34-37 (2003).

Lin, T. H., "Implementation and characterization of a flexure-beam micromechanical spatial light modulator," Optical Engineering, 33(11): 3643-3648 (1994).

Lin, W. C., et al., "On Dual Ultrasound Sensor Technique for Unmanned Vehicles," Automation in Construction, 1(2): 153-165 (1992).

Link, S. and El-Sayed, M. A. "Spectral properties and relaxation dynamics of surface plasmon electronic oscillations in gold and silver nanodots and nanorods," Journal of Physical Chemistry B, 103(40): 8410-8426 (1999).

Lipson, A., and Yeatman, E. M., "A 1-D photonic band gap tunable optical filter in (110) Silicon," Journal of Microelectromechanical Systems, 16(3): 521-527 (2007).

Liu, H., and Milios, E., "Acoustic positioning using multiple microphone arrays," Journal of the Acoustical Society of America, 117(5): 2772-2782 (2005).

Love, G. D., et al., "Liquid-crystal prisms for tip-tilt adaptive optics," Optics Letters, 19(15): 1170-1172 (1994).

Lu, W., et al., "Photoacoustic imaging of living mouse brain vasculature using hollow gold nanospheres," Biomaterials, 31(9): 2617-2626 (2010).

M. Han, X. Wang, J. Xu, K. L. Cooper, and A. Wang, "Diaphragm-based extrinsic Fabry-Perot interferometric optical fiber sensor for acoustic wave detection under high background pressure", Optical Engineering, vol. 44, No. 6, pp. 060506-2, 2005.

Ma, X., et al., "Surface-Enhanced Raman Scattering Sensor on an Optical Fiber Probe Fabricated by a Femtosecond Laser," Sensors, 10:11064-11071 (2010).

Maslov, K., et al., "Optical-resolution photoacoustic microscopy for in vivo imaging of single capillaries," Optics letters, 33(9): 929-931 (2008).

Masotti, L., et al., "FEMMINA—A Fast Echographic Multi-Parametric Multi-Imaging Novel Apparatus," in Proceedings IEEE International Ultrasonics Symposium, pp. 739-748 (1999).

Masotti, L., et al., "Ultrasonic Images of Tissue Local Power Spectrum by Means of Wavelet Packets for Prostate Cancer Direction," Acoustic Imaging (2002).

Matic, R. M. "Blazed phase liquid crystal beam steering", Laser Beam Propagation and Control, Los Angeles, CA, USA, pp. 194-205, 1994.

Maxfield, B. and Fortunko, C.M., "The Design and Use of EMAT's," Materials Evaluation, 41(10): S26 (1983).

Maxfield, B. W. et al., "Evaluating EMAT Designs for Selected Applications," Materials Evaluation, 45: 1166-1182 (1987).

McGee, J., et al., "In-plane indium phosphide tunable optical filter using ridge Waveguides," Semiconductor Device Research Symposium, pp. 56-57 (2005).

McLaughlan, J. R., et al., "Ultrasonic enhancement of photoacoustic emissions by nanoparticle-targeted cavitation," Optics Letters, 35(13): 2127-2129 (2010).

McRuer, R., et al., "Ferroelectric liquid-crystal digital scanner," Optics Letters, 15(23): 1415-1417 (1990).

Menichelli, D., et al., "Optoacuostic Sources: A Practical Green Function-Based Model for Thin Film Laser-Ultrasound Generation," Journal of Optics A: Pure and Applied Optics, 3(4): S23 (2001).

Metzger, C. H., and Karrai, K., "Cavity cooling of a microlever," Nature, 432(7020): 1002-1005 (2004).

Mi, B., "Implementation of fiber phased array ultrasound generation system and signal analysis for weld penetration control," In Partial Fulfillment of the Requirements for the Degree Doctor of Philosophy in School of Mechanical Engineering, Georgia Institute of Technology (2003).

Milster, T. D., and Wong, J. N., "Modeling and measurement of a micro-optic beam Deflector," Proceedings of SPIE, 1625: 78 (1992).

Mitchel, J. F., et al., "Intracardiac ultrasound imaging during transseptal catheterization," Chest, 108: 104-8 (1995).

Mukherjee, S., et al., "An Efficient Silver Etchant for the Fabrication of Active Nanowires Using Anodized Aluminum Oxide Templates," Electrochemical and Solid-State Letters, 13(7): D50-D52 (2010).

Murray, P. R. and Dewhurst, R. J. , "A Laser/EMAT System for Thickness Monitoring Applications Using Shear and L-S Mode-Converted Waves," Measurement Science and Technology, 12: 1651-1659 (2001).

Nan Wu, Wenhui Wang, Ye Tian, Charles Guthy and Xingwei Wang, "Theoretical analysis of a novel ultrasound generator on an optical fiber tip", Proceeding of SPIE, vol. 7677, 76770X, 2010.

Nissen, S.E., et al., "Intravascular Ultrasound: Novel Pathophysiological Insights and Current Clinical Applications," Circulation, 103(4): 604-616 (2001).

Notification Concerning Transmittal of International Preliminary Report on Patentability for International Application No. PCT/US2012/025646; "Photoacoustic Probe", Date Mailed: Aug. 29, 2013.

NSF, "National Science Board Science and Engineering Indicators," Chapter. 2 (2008).

NSF, "The Engineering Workforce: Current State, Issues, and Recommendations, Final Report to the Assistant Director of Engineering," (2005).

Oksanen, M., and Wu, J., "Prediction of the temporal shape of an ultrasonic pulse in a photoacoustic sensing application," Ultrasonics, 32: 43-46 (1994).

Olgin, J. E., et al., "Electrophysiological effects of long, linear atrial lesions placed under intracardiac ultrasound guidance," Circulation, 96: 2715-2721 (1997).

Olson, E. S., "Observing middle and inner ear mechanics with novel intracochlear pressure Sensors," Journal of the Acoustical Society of America, 103(6): 3445-3463 (1998).

Oraevsky, A. A., et al., "Measurement of tissue optical properties by time-resolved detection of laser-induced transient stress," Applied Optics, 36(1): 402-415 (1997).

Oralkan, O., et al., "Capacitive Micromachined Ultrasonic Transducers: Next-Generation Arrays for Acoustic Imaging?" IEEE Transactions on Ultrasonics, Ferroelectrics and Frequency Control, 49 (11): 1596-1610 (2002).

Oralkan, O., et al., "Volumetric Imaging Using 2D Capacitive Micromachined Ultrasonic Transducer Arrays (CMUTS): Initial Results", In Proceedings IEEE International Ultrasonics-Symposium, pp. 1083-186, vol. 2., (2002).

Packer, D. L., et al., "Intracardiac phased-array imaging: methods and initial clinical experience with high resolution, under blood visualization: Initial experience with intracardiac phased-array ultrasound," Journal of the American College of Cardiology, 39 (3): 509-516 (2002).

Petrova, H., et al., "Photothermal Properties of Gold Nanoparticles," Zeitschrift für Physikalische Chemie, 221(3): 361-376 (2007).

(56) References Cited

OTHER PUBLICATIONS

Resler, D. P., et al., "High-efficiency liquid-crystal optical phased-array beam steering," Optics Letters, 21(9): 689-691 (1996).
Reverdy, F., and Audoin, B., "Ultrasonic measurement of elastic constants of anisotropic materials with laser source and laser receiver focused on the same interface," Journal of Applied Physics, 90(9): 4829-4835 (2001).
Roome, K. A., et al., "Towards a Sideways Looking Intravascular Laser-Ultrasound Probe," Sensors and Actuators A: Physical, 76(1-3): 197-202 (1999).
Royer, D., and Dieulesaint, E., "Influence of the elastic properties of the backing material in thermoelastic wave generation," in Proceedings IEEE International Ultrasonics Symposium, pp. 664-667 (1983).
Saadany, B., et al., "Free-space tunable and drop optical filters using vertical Bragg mirrors on silicon," IEEE Journal of Selected Topics in Quantum Electronics, 12(6): 1480-1488 (2006).
Said, A. A., et al., "Carving Fiber-Top Cantilevers With Femtosecond Laser Micromachining," Journal of Micromechanics and Microengineering, 18(3): 035005 (2008).
Sassaroli, E., et al., "Numerical investigation of heating of a gold nanoparticle and the surrounding microenvironment by nanosecond laser pulses for nanomedicine applications," Physics in Medicine and Biology, 54: 5541-5560 (2009).
Savateeva, E. V., et al., "Noninvasive detection and staging of oral cancer in vivo with confocal optoacoustic tomography," Biomedical Optoacoustics, San Jose, CA, USA, 3916, pp. 55-66 (2000).
Schulz, L.G., "The Optical Constants of Silver, Gold, Copper and Aluminum. I. The Absorption Coefficient k," J. Opt. Soc. Am., 44(5); 357-362 (1954).
Schulz, L.G., et al., "Optical Constants of Silver, Gold, Copper and Aluminum. II. The Index of Refraction n," J. Opt. Soc. Am., 44(5); 362-367 (1954).
Schwartz, S. L., et al., "Intracardiac echocardiography in humans using a small-sized (6F), low frequency (12.5 MHz) ultrasound catheter: Methods, imaging planes and clinical experience," Journal of the American College of Cardiology, 21: 189-198 (1993).
Sharp, G., and Johnson, K., "High speed analog complex-amplitude liquid crystal light Modulator," Optics Letters, 19(16) 1994.
Shinn-Cunningham, B., "Localizing sound in rooms," Proceedings of the ACM Siggraph and Eurographics Campfire: Acoustic Rendering for Virtual Environments, Snowbird, Utah, pp. 17-22 (2001).
Smith, K., et al., "Fiber-Top Atomic Force Microscope: A Worthwhile Challenge," Opto-Electronics and Communications Conference, 2008 and the 2008 Australian Conference on Optical Fibre Technology, pp. 1-4 (2008).
Spencer, T., et al., "Characterization of Atherosclerotic Plaque by Spectral Analysis of Intravascular Ultrasound: An Invitro Methodology," Ultrasound in Medicine and Biology, 23(2): 191-203 (1997).
Stearns, R. G., and Kino G. S., "Effect of electronic strain on photoacoustic generation in Silicon," Applied Physics Letters, 47(10): 1048-1050 (1985).
Stievater, T. H., et al., "All-optical micromechanical chemical sensors," Applied Physics Letters, 89(9): 091125-3 (2006).
Sun et al., "Simulation on photoacoustic conversion efficiency of optical fiber-based ultrasound generator using different absorbing film materials" SPIE Smart Structures/NDE (2011).
Sun, K., et al., "Finite Element Modeling of an Optical Fiber Photoacoustic Generator Performance," SPIE Smart Structures/NDE, (2011).
Swift, C. I., et al., "Laser generated ultrasound using directly coated fibre optic Patchcords," Electronics Letters, 36(25): pp. 2113-2114 (2000).
Tam, A. C., "Applications of photoacoustic sensing techniques", Reviews of Modern Physics, 58(2): 381 (1986).
Telschow, K. L., and Conant, R. J., "Optical and thermal parameter effects on laser-generated ultrasound," Journal of the Acoustical Society of America, 88: 1494-1502 (1990).
Thompson, R. B., "New EMAT Configuration for Generating Sh-Waves in Ferromagnetic Materials," IEEE Transactions on Sonics and Ultrasonics, 26(2): 149 (1979).
Totsu, K., et al., "Ultra-miniature fiber-optic pressure sensor using white light Interferometry," Journal of Micromechanics and Microengineering, 15: 71-75 (2005).
Tung, T.L., et al., "Source localization and spatial filtering using wideband music and maximum power beamforming for multimedia applications," IEEE Workshop on Signal Processing Systems, pp. 625-634 (1999).
Vakarelski, I. U., et al., "Thermal modification of layer-by-layer assembled gold nanoparticle films," Colloids and Surfaces A:Physicochemical and Engineering Aspects, 340(1-3): 193-198 (2009).
Viadero, D., "Researchers Mull STEM Gender Gap," Published Online. http://www.edweek.org/ew/index.html, 2009.
Vogel, J. A.., et al., "Beamsteering of laser generated ultrasound," Proceedings of Ultrasonics International, Butterworth, Washington, D. C., pp. 141-152 (1987).
Von Gutfeld, R. J., "Thermoelastic generation of elastic waves for non-destructive testing and medical applications," Ultrasonics, 18: 175-181 (1980).
Von Gutfeld, R. J., "Thermoelastically Generated MHz Elastic Waves from Constrained Surfaces," in Proceedings IEEE International Ultrasonics Symposium, pp. 397-402 (1977).
Von Gutfeld, R. J., and Melcher, R. L., "20-MHz acoustic waves from pulsed thermoelastic expansions of constrained surfaces," Applied Physics Letters, 33: 175-181 (1980).
Wang, W., and Wang, X., "Label-Free Fiber Optic Biosensor With Single PMMA Functional Layer," International Conference on Optical Fibre Sensors, Western Australia, (2008).
Wang, W., et al., "Optical Interferometric Biosensor With PMMA as Functional Layer," Fall Meeting of Material Research Society, Boston, 1133-AA03-02 (2008).
Wang, W., et al., "Surface-enhanced Raman scattering on optical material fabricated by femtosecond laser," Proceeding of SPIE, Defense, Security, and Sensing, Orlando, FL, USA (Apr. 5-9, 2010).
Wang, W., et al., "Surface-enhanced-raman-scattering on quartz substrate and optical fiber with nanostructures fabricated by femtosecond laser," Fall meeting of Material Research Society, Boston (2008).
Wang, X., and Li, D., "Comparison of IC-Engine Pressure Sensor Technologies and Their Prospects," Diesel Engine, pp. 20-33 (2003).
Wang, X., et al., "Diaphragm design guidelines and an optical pressure sensor based on MEMS technique," Microelectronics Journal, 37(1): 50-56, 1, (2006).
Wang, X., et al., "Implementation of Nondestructive Young's Modulus Measurement by Miniature Optical Sensors," SPIE OpticsEast—Sensors for Harsh Environments, Boston, MA, 5998, 599805 (2005).
Wang, X., et al., "All-fused-silica miniature optical fiber tip pressure sensor," Optics Letters, 31(7): 885-887 (2006).
Wang, X., et al., "An optical fiber tip pressure sensor for medical applications," Quantum Electronics and Laser Science Conference, pp. 916-918 (2006).
Wang, X., et al., "Label-Free DNA Detection on the Surface of an Optical Fiber Tip," Conference on Lasers and Electro-Optics/Quantum Electronics and Laser Science Conference (CLEO/QELS), Long Beach, CA, pp. CMR3 (2006).
Wang, X., et al., "Miniature Optical Fiber Sensor for Dynamic Pressure Measurements Under High Background Pressure," Optics and Photonics, San Diego, CA (2006).
Wang, X., et al., "Noninvasive laser-induced photoacoustic tomography for structural and functional in vivo imaging of the brain," Nature Biotechnology, 21(7): 803-806 (2003).
Wang, X., et al., "Study on the layer-by-layer electrostatic self assembly method for biomolecule immobilization onto biosensor surface," Nanocoatings, San Diego, CA, USA, 6647, 66470G-9 (2007).

(56) References Cited

OTHER PUBLICATIONS

Wang, X., et al., "Verifying an All Fused Silica Miniature Optical Fiber Tip Pressure Sensor Performance With Turbine Engine Field Test," SPIE OpticsEast—Sensors for Harsh Environments, Boston, MA, pp. 23-26 (2005).

Wang, Z., et al., "Optical High DC Voltage Sensor Based on White-Light Interferometry," IEEE Photonics Technology Letters, 18 (19): 2002-2004 (2006).

Watson, E. A., "Analysis of beam steering with decentered microlens arrays," Optical Engineering, 32: 2665-2670 (1993).

Watson, R. J., et al., "Classification of Arterial Plaque by Spectral Analysis of In Vitro Radio Frequency Intravascular Ultrasound Data,"Ultrasound in Medicine and Biology, 26 (1): 73-80 (2000).

Wei, M., et al., "Directed Assembly of Polymer Blends Using Nanopatterned Templates," Advanced Materials, 21(7): 794-798 (2009).

Wei, M., et al., "Fabrication of Patterned Conducting Polymers on Insulating Polymeric Substrates by Electric-Field-Assisted Assembly and Pattern Transfer," Macromolecular Rapid Communications, 27(21): 1826-1832 (2006).

Wetsel, G. C., "Photothermal generation of thermoelastic waves in composite media," IEEE Transactions on Ultrasonics, Ferroelectrics and Frequency Control, 33(5): 450-461 (1986).

Wetsel, G., "Thermoelastic wave generation by the heated interface between two media," in Proceedings IEEE International Ultrasonics Symposium, pp. 645-648 (1980).

White, R. M., "Generation of elastic waves by transient surface heating," Journal of Applied Physics, 34(12): 3559-3567 (1963).

Wilkens, V., and Koch, C., "Fiber-optic multilayer hydrophone for ultrasonic Measurement," Ultrasonics, 37(1): 45-49 (1999).

Wu, N., et al., "Fiber Optics Photoacoustic Generation Using Gold Nanoparticles as Target," SPIE Smart Structures/NDE, (2011).

Wu, S. T., "Room temperature diphenyl-diacetylene liquid crystals," Applied Physics Letters, 61: 630 (1992).

Wu, S. T., and Wu, C. S., "Experimental confirmation of the Osipov-Terentjev theory on the viscosity of nematic liquid crystals," Physical Review Letters, 42(4): 2219-2227 (1990).

Wu, S. T., et al., "Physical properties of diphenyl-diacetylenic liquid crystals," Journal of Applied Physics, 65: 4372 (1989).

Xu, J., et al., "High-Temperature Thermometer With Fiber Optic Readout," SPIE OpticsEast—Sensors for Harsh Environments, Boston, MA, 5998, 59980B (2005).

Xu, J., et al., "Vacuum-Sealed High Temperature High Bandwidth Fiber Optic Pressure and Acoustic Sensors," SPIE OpticsEast—Sensors for Harsh Environments, Boston, MA, 5998, 599809 (2005).

Xu, J., et al., "A Novel Temperature-Insensitive Optical Fiber Pressure Sensor for Harsh Environments," IEEE Photonics Technology Letters, 17(4): 870-872 (2005).

Xu, J., et al., "Epoxy-Free High Temperature Fiber Optic Pressure Sensors for Gas Turbine Engine Applications," SPIE OpticsEast—Sensors for Harsh Environments, Philadelphia, PA: pp. 1-10 (2004).

Xu, J., et al., "Miniature All-Silica Fiber Optic Pressure and Acoustic Sensors," Optics Letters, 30 (24): 3269-3271 (2005).

Xu, J., et al., "Miniature Fiber Optic Pressure and Temperature Sensors," SPIE OpticsEast—Sensors for Harsh Environments, Boston, MA, 6004, 600403 (2005).

Xu, J., et al., "Miniature Temperature-Insensitive Fabry-Perot Fiber-Optic Pressure Sensor," IEEE Photonics Technology Letters, 18(10): 1134-1336 (2006).

Xu, L., et al., "Noncovalent Nonspecific Functionalization and Solubilization of Multi-Walled Carbon Nanotubes at High Concentrations with a Hyperbranched Polyethylene," Macromolecular Chemistry and Physics, 210(24): 2194-2202 (2009).

Xu, M., and Wang, L.V., "Analytic explanation of spatial resolution related to bandwith and detector aperture size in thermoacoustic or photoacoustic reconstrcution," Physcial Review E, 67(5) 056605 (2003).

Yang, X., et al., "Nanoparticles for photoacoustic imaging," Wiley Interdisciplinary Reviews: Nanomedicine and Nanobiotechnology, 1(4): 360-368 (2009).

Yock, P.G., et al., "Intravascular Ultrasound: State of the Art and Future Directions," The American Journal of Cardiology, 81 (7, Supplement 1): 27E-32E (1998).

York, E. A., "Gender Differences in the College and Career Aspirations of High School Valedictorians," Journal of Advanced Academics, 19: 578-600 (2008).

Yu, M., "Biology-inspired miniature optical directional microphones: Bridging biological systems and sensor technology," NSF Program(s): Sensors and sensing systems, Award Abstract #: 0644914 (2007).

Yu, M., and Balachandran, B., "Acoustic measurements using a fiber optic sensor system," Journal of Intelligent Material Systems and Structures, 14(7): 409-414 (2003).

Zhang, H. F., et al., Imaging of Hemoglobin Oxygen Saturation Variations in Single Vessels In Vivo Using Photoacoustic Mircoscopy, Applied Physics Letters, 90(5): 053901-N.PAG (2007).

Zhang, H.F., et al., "In vivo imaging of subcutaneous structures using functional photoacoustic microscopy," Nature Protocols, 2(4): 797-804 (2007).

Zhang, H.F., et al., "Functional photoacoustic microscopy for high-resolution and noninvasive imaging," National Biotechnology, 24(7): 848-51 (2006).

Zharov, V. P., et al., "Photothermal detection of local thermal effects during selective nanophotothermolysis," Applied Physics Letters, 83(24): 4897-4899 (2003).

Zhou, S., et al., "Finite-element analysis of material and parameter effects in laser-based thennoelastic ultrasound generation," IEEE Transactions on Ultrasonics, Ferroelectrics and Frequency Control, 51(9): 1178-1186 (2004).

Chandrasekaran, S. and Sundararajan, S., "Effect of microfabrication processes on surface roughness parameters of silicon surfaces", Proceedings of the 31st International Conference on Metallurgical Coatings and Thin Films, 188-189: 581-587 (Nov.-Dec. 2004).

Chen, X. et al., "Deep wet etching on fused silica material for fiber optic sensors", Proc. SPIE, 5342: Abstract (Dec. 30, 2003).

Gander, M. J., et al., "Embedded Micromachined Fiber-Optic Fabry-Perot Pressure Sensors in Aerodynamics Applications", IEEE Sensors Journal, 3(1): 102-107 (Feb. 2003).

Kim, Y. and Neikirk, D.P., "Micromachined Fabry-Perot cavity pressure transducer", Photonics Technology Letters, IEEE, 7(12): 1471-1473 (Dec. 1995).

Lee, J-R. and Tsuda, H., "A novel fiber Bragg grating acoustic emission sensor head for mechanical tests", Scripta Materialia, 53: 1181-1186 (2005).

Wang, W. et al., "Miniature all-silica optical fiber pressure sensor with an ultrathin uniform diaphragm", Optics Express, 18(9): 9006-9014 (Apr. 14, 2010).

Wang, X. et al., "An ultra-sensitive optical MEMS sensor for partial discharge detection", Journal of Micromechanics and Microengineering, 15: 521-527 (2005).

Xu, J. et al., "Miniature all-silica fiber optic pressure and acoustic sensors", Optics Letters, 30(24): 3269-3271 (Dec. 15, 2005).

Supplementary Partial European Search Report, mailed Apr. 14, 2016 in European Application No. EP 12746867, entitled "Photoacoustic Probe".

Boonsang, S., and Dewhurst, R. J. , "A Sensitive Electromagnetic Acoustic Transducer for Picometer-Scale Ultrasonic Displacement Measurements," Sensors and Actuators A: Physical, 127 (2): 345-354 (2006).

Extended European Search Report, "Photoacoustic Probe," date of mailing Aug. 16, 2016.

Fatemi, M., and Greenleaf, J. F., "Ultrasound-stimulated vibroacoustic spectrography," Science, 280(5360): 82-85 (1998).

Huang, J., et al., "Sound localization in reverberant environment based on the model of the precedence effect," IEEE Transactions on Instrumentation and Measurement, 46(4): 842-846 (1997).

Huber, T. M., et al., "Noncontact Modal Testing of Hard-Drive Suspensions Using Ultrasound Radiation Force," Journal of the Acoustical Society of America, 118: 1928 (2005).

(56) References Cited

OTHER PUBLICATIONS

Lee, R. J., et al., "Radiofrequency catheter modification of the sinus node for "inappropriate" sinus tachycardia," Circulation, 92: 2919-2928 (1995).

Olgin, J. E., et al., "Role of right atrial endocardial structures as barriers to conduction during human type Iatrial flutter: Activation and entrainment mapping guided by intracardiac echocardiography," Circulation, 92: 1839-1848 (1995).

Reid, G. L., and Milios, E., "Active stereo sound location, " Journal of the Acoustical Society of America, 113: 185-193 (2003).

Ren, J. F., et al., "Intracardiac catheter echocardiographic (9MHz) imaging: in vivo validation and initial clinical applications (abstr)," Journal of the American Society of Echocardiography, 10: 406 (1997).

Wang, L. V., "Prospects of photoacoustic tomography," Medical Physics, 35(12): 5758-5767 (2008).

Wang, W., et al., "Fabry Perot Optical Fiber Pressure/Acoustic Sensor With Accurate Cavity Length Control," vol. 1 The 7th International Workshop on Structural Health Monitoring 2009 from System integration to Autonomous Systems, Stanford University, Stanford, CA (2009), pp. 949-956.

Wang, Z., et al., "Multiplexed Fiber Fabry-Perot Interferometric Sensor Based on Wideband Bragg Gratings," IEEE Photonics Technology Letters,19 (8): 622-624 (2007).

Zhu, Y., et al., "Miniature Fiber-Optic Pressure Sensor for Turbine Engine," SPIE OpticsEast—Sensors for Harsh Environments, Philadelphia, PA: pp. 11-18 (2004).

International Preliminary Report on Patentability mailed Jan. 12, 2012 of International Application No. PCT/US2010/040460, "Optical Fiber Pressure Sensor With Uniform Diaphragm and Method of Fabricating Same", International Filing Date Jun. 29, 2009.

International Search Report and Written Opinion mailed Oct. 14, 2010 of International Application No. PCT/US2010/040460, "Optical Fiber Pressure Sensor With Uniform Diaphragm and Method of Fabricating Same", International Filing Date Jun. 29, 2009.

NonFinal Office Action for U.S. Appl. No. 13/381,256, entitled: "Optical Fiber Pressure Sensor With Uniform Diaphragm and Method of Fabricating Same," Date Mailed Mar. 8, 2016.

Notice of Allowance for U.S. Appl. No. 13/381,256, entitled: "Optical Fiber Pressure Sensor With Uniform Diaphragm and Method of Fabricating Same," Date Mailed Aug. 8, 2016.

Supplemental Notice of Allowability, U.S. Appl. No.: 13/381,256, "Optical Fiber Pressure Sensor With Uniform Diaphragm and Method of Fabricating Same," dated Sep. 28, 2016.

\* cited by examiner

The acoustic signals generated by the gold nanocomposite.

PHOTOACOUSTIC PROBE

RELATED APPLICATION(S)

This application is the U.S. National Stage of International Application No. PCT/US2012/025646, filed Feb. 17, 2012, which designates the U.S. published in English, and claims the benefit of U.S. Provisional Application No. 61/443,925, filed on Feb. 17, 2011.

The entire teachings of the above applications are incorporated herein by reference.

BACKGROUND OF THE INVENTION

Most ultrasound detection systems are based on piezoelectric, electromagnetic or capacitive effects. Typically, they have inherent difficulty in achieving broad bandwidth, high frequency, miniaturization and safety. Optical ultrasound technology has been applied to provide simplified structure, reduced size improved biocompatibility and higher frequency. Several optical ultrasound technologies have been proposed. However, most such proposals operate under a simplex scheme whereby ultrasound is generated, or detected, but not both. Further, most parameters of such probes, such as signal-to-noise ratio, resolution, penetration depth, focus point, and direction, are preset during fabrication.

Therefore, a need exists for a probe that minimizes or overcomes the above mentioned problems.

SUMMARY OF THE INVENTION

The present invention generally relates to a photoacoustic probe that both generates ultrasonic waves by modulated optical radiation and detects reflections of that ultrasonic radiation by a Fabry-Perot (FP) cavity component within the probe.

In one embodiment, a photoacoustic probe of the invention includes an optical fiber, a diaphragm at the optical fiber whereby the optical fiber and the diaphragm define a cavity, and an energy absorption film at the optical fiber. An activating laser directed through the optical fiber can excite the energy absorption film to thereby generate an acoustic wave that, upon reflection from a remote surface, can deflect the diaphragm and modify reflection of a detecting laser that is also directed through the optical fiber.

In another embodiment, the invention is a method of detecting an acoustic wave, including the steps of directing an activating laser through an optical fiber to an energy absorption film at the optical fiber to thereby generate an acoustic wave, and directing a detecting laser through the optical fiber and a cavity to a diaphragm at the optical fiber, the cavity being defined by the optical fiber and the diaphragm. An interference pattern generated at least in part by reflection of the detecting laser from a surface of the diaphragm is measured and is indicative of the reflection of the acoustic wave from a remote surface.

This invention has many advantages. For example, the photo acoustic probe of the invention can be employed as a replacement for traditional ultrasonic probes employed in echography, such as is employed to conduct spectral analysis of in-vivo tissues, coronary arteries, skin tumors and the prostate glands. Further, probes can be employed in diagnosing misplacement of stents during coronary intravascular ultrasound procedures and, because the probes can be of very small size, they can be employed where limited space is available to thereby provide autonomous intelligence generally not provided by robotics/bio-mimic systems or surveillance systems of unmanned miniature vehicles. Further, the photoacoustic probe of the invention can be employed in environments that are chemically or electrically hazardous or in high temperature conditions during, for example, real-time structural health monitoring and material characterization. Further, the photoacoustic probe of the invention can be employed in strong magnetic or electrical environments, such as magnetic resonance imaging (MRI) machines, where electrical counterparts are not compatible.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

The present invention generally is directed to an optical fiber tip that integrates an all-optical ultrasonic generator module and receiver module. The optical fiber tip, as a photoacoustic probe, employs a phased-array technique to control directionality and focus of ultrasonic waves toward a target.

Photoacoustics are employed to generate ultrasonic waves by modulated optical radiation. In an "unconfined" approach, laser energy is exerted directly onto a target to generate ultrasound. Examples of suitable targets include composites, liquids, silicon and biological tissues. One possible limitation of such techniques is thermal damage to the target. In an alternative, "confined" approach, a thin absorbing film, such as a thermoelastic material, is employed to absorb optical radiation and thereby generate ultrasonic waves that propagate toward the target. The invention employs the confined approach.

Figure 1A:
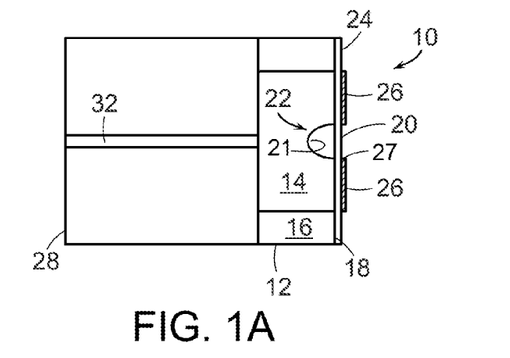
FIGS. 1A and 1B are cross-sectional end and views, respectively, of one embodiment of a photoacoustic probe of the invention.

One embodiment of a photoacoustic transducer of the invention is represented in FIG. 1A. As shown therein, photoacoustic transducer 10 includes multimode fiber 12. Multimode fiber 12 includes core 14 and cladding 16. An example of a suitable cladding material includes silicon dioxide. Core 14 of multimode fiber 12 typically are formed of the same material, but core 14 is doped with a suitable dopant, such as gemanium (Ge). Alternatively, the cladding is doped with fluorine (F) and the core is essentially pure silicon dioxide. The diameter of multimode fiber 12 of photoacoustic transducer 10 typically is in a range of between about 125 µm and about 800 µm. Typically, the diameter of core 14 of multimode fiber 12 is in a range of between about 50 µm and about 600 µm. However, the size of both fibers can be further tapered down to micrometer size; or bigger sizes of the fibers can be used if necessary. The thickness (t) of multimode fiber 12 typically is in a range of about between 30 µm and about 200 µm. Multimode fiber 12 includes first planar surface 18, which typically is orthogonal to a major longitudinal axis of photoacoustic transducer 10.

Diaphragm 20 is bonded to first surface 18. Diaphragm 20 is typically formed of silicon dioxide, silicon nitride or a polymer, such as polydimethylsiloxane (PDMS), epoxy, or polymethylmethacrylate (PMMA). In one embodiment, diaphragm 20 is fabricated by growing an oxide layer on a silicon wafer, followed by etching away a silicon wafer. A silicon substrate is used to grow an oxide layer. Certain thickness of the silicon dioxide layer can be controlled precisely by monitoring the growing time. The silicon dioxide diaphragm is released by back etching away the silicon through wet etching or dry etching methods. The wet etching involves potassium hydroxide (KOH) solution and the dry etching involves deep reactive-ion etching (RIE).

A diaphragm of silicon nitride can be fabricated in a similar manner, wherein a nitride layer is grown on a surface of a silicon wafer, followed by etching away the silicon wafer. Generally, diaphragm 20 has a thickness in a range of between about 0.5 µm and about 30 µm or between about 1 um and about 10 um. Further, diaphragm 20 is bonded to first surface 18 by a suitable method, such as thermally bonding using laser or torch.

Diaphragm 20 can be bonded to surface 18 of multimodal fiber 12 by a suitable technique, such as thermal bonding, laser bonding or chemical synthesis, as is known in the arts. For example, thermal bonding is conducted by heating diaphragm 20 and multimodal fiber 12 until they are both partially melted and then bonded together. Laser bonding can be conducted by locally heating the diaphragm and the fiber to bond them together. Chemical synthesis generally is employed to bond a polymer diaphragm, which can be synthesized directly over recessed portion 21.

Fabry-Perot cavity 22 is defined by recessed portion 21 of core 14 and diaphragm 20. Typically, depth (d) of Fabry-Perot cavity 22 is in a range of between about 5 µm and about 100 µm and has a width (w) in a range of between about 10 µm and about 600 µm.

Figure 1B:
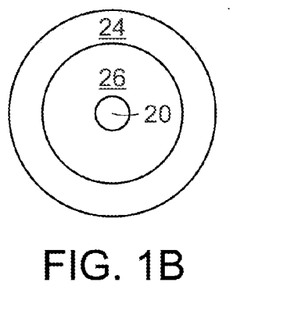

Diaphragm 20 includes surface 24. Energy absorption film 26 is bonded to surface 24 of diaphragm 20. Energy absorption film 26 can be any suitable energy absorption film known to convert optical radiation to ultrasonic radiation. As can be seen in FIG. 1B, energy absorption film defines opening 27 at diaphragm 20. Typically, energy absorption film 26 has a thickness in a range of between about 0.5 µm and about 800 µm.

An example of a suitable material of energy absorption film 26 includes graphite mixed within curable polymers such as PDMS or epoxy, or some other suitable material having a relatively high coefficient of thermal expansion (CTE), a relatively high optical absorption co-efficient and high temperature survivability. In one embodiment of the present invention, gold nanoparticles are combined with graphite or gold nanoparticles alone mixing within curable polymers such as PDMS or epoxy to form an absorbing film of a photoacoustic probe. In a specific embodiment, the gold nanoparticles include gold nanorods, preferably having an aspect ratio in a range between about 1.0 and about 6.5 and, optimally, an effective radius in a range of from about 8 nm to about 25 nm. Alternatively, gold nanospheres, having a diameter in the range of between about 10 nanometers to about 100 nanometers, are employed. In still another embodiment, the nanoparticles can be in the form of nanoshells having a total radius, for example, in a range from about 50 nm to about 150 nm, and a core/shell ratio in a range of from about 0.1:1 to about 1:1.

Multimode fiber 12 generally is formed by bonding a multimode fiber to single mode fiber 28 by a suitable technique, such as fusion splicing.

Figure 2A:
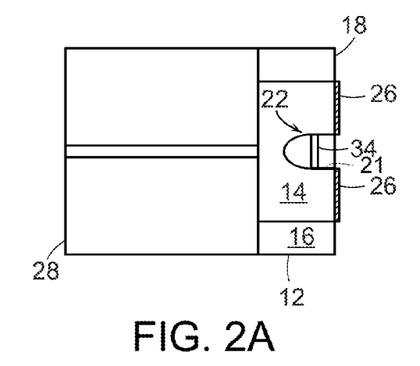
FIGS. 2A and 2B are cross-sectional and end views, respectively, of another embodiment of the photoacoustic probe of the invention.
Figure 2B:
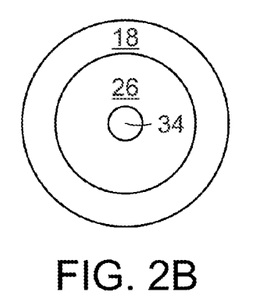

In another embodiment of the invention, shown in FIGS. 2A and 2B, diaphragm 34 is recessed within Fabry-Perot cavity 22. Diaphragm 34 is bonded to core 14 of multimode fiber 12 by the same method as that employed to fabricate the embodiment shown in FIGS. 1A and 1B.

Figure 3A:
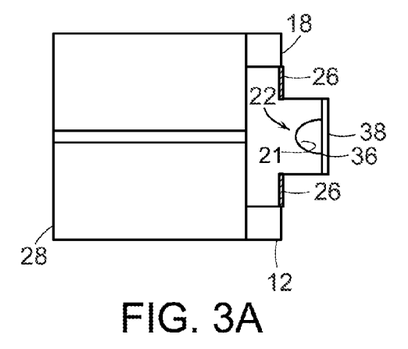
FIGS. 3A and 3B are cross-sectional and end views, respectively, of still another embodiment of the photoacoustic probe of the invention.
Figure 3B:
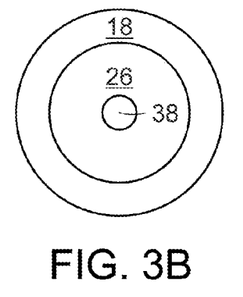

In still another embodiment, as shown in FIGS. 3A and 3B, second surface 36 is raised from first surface 18. Diaphragm 38 is bonded to second surface 36.

Figure 4A:
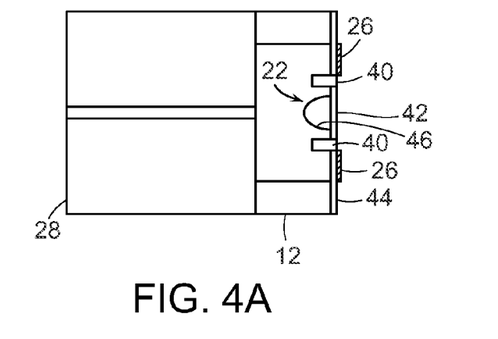
FIGS. 4A and 4B are cross-sectional and end views, respectively, of still another embodiment of the photoacoustic probe of the invention.
Figure 4B:
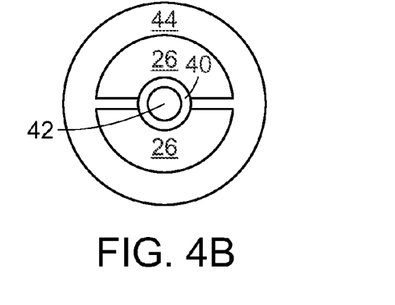

In yet another embodiment, shown in FIGS. 4A and 4B, trench 40 partitions energy absorption film 26 from portion 42 of diaphragm 44 that, in combination with recessed portion 46 of core 14 of multimode fiber 12, defines Fabry-Perot cavity 22. Trench 40 can be formed employing the same technique as that employed to form recessed portion 46. For example, trench 40 can be formed by wet etching with 49% hydrofluoric acid (HF). Alternatively, trench 40 can be fabricated by use of a focused ion beam (FIB).

Suitable trenches may have a width in a range of between about 1 micrometer and about 120 micrometers. In one example, trench 40 may have a width in a range of between about 1 micrometer and about 10 micrometers. Trench 40 may have a depth in a range of between about 1 micrometer and about 30 micrometers. In one example, trench 40 may have a depth in a range from about 1 to about 20 micrometers.

Figure 5A:
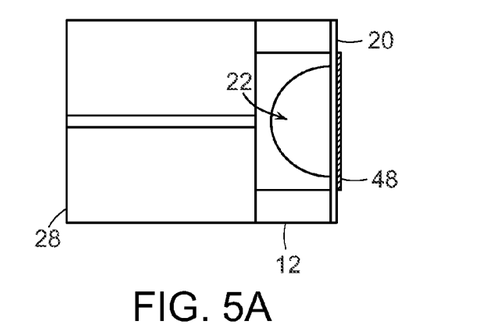
FIGS. 5A and 5B are cross-sectional and end views, respectively, of still yet another embodiment of the photoacoustic probe of the invention.
Figure 5B:
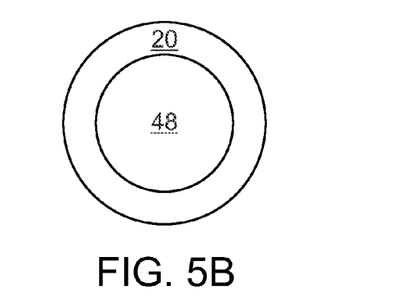

Trench 40 is employed to minimize cross-talk between acoustic waves generated by energy absorption film and reflected waves that are detected by deflection of diaphragm 44. In one embodiment, for example, the photoacoustic transducer of the invention can be fabricated from an optical fiber having a diameter of about 125 micrometers. Generally speaking, the diameter of the photoacoustic transducer is much smaller than the wavelength of ultrasonic waves (e.g., about 1.5 millimeters for about 1 MHz). If diaphragm 44 has a diameter of about 5 micrometers and a thickness of 0.3 micrometers, the resonant frequency is 80 MHz and the sensitivity is 0.01 nm/kPa. In one embodiment, cantilever having a length of about 112 micrometers, a width of about 14 micrometers and a thickness of 3.7 micrometers have been fabricated that are anchored to a fiber having a diameter of 125 micrometers. In an alternate embodiment, FIB has been employed to mill a trench in the form of a ring 80 micrometers in diameter, 3 micrometers in width and about 4.5 micrometers in depth. Another embodiment, shown in FIGS. 5A and 5B, include energy absorption film 48 covering diaphragm 20 at Fabry-Perot cavity 22. Alternatively, energy absorption film 48 might only partially cover diaphragm 24 at Fabry-Perot cavity 56.

Figure 6A:
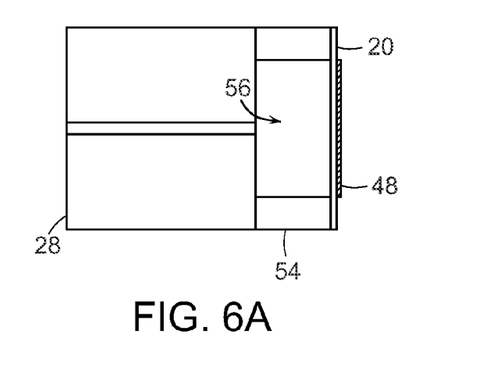
FIGS. 6A and 6B are cross-sectional and end views, respectively, of another embodiment of the photoacoustic probe of the invention.
Figure 6B:
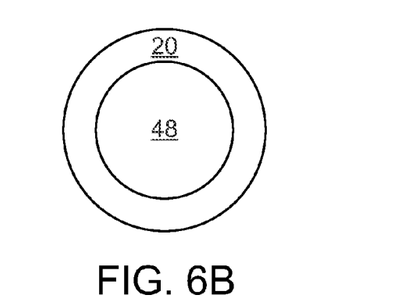

In still another embodiment, shown in FIGS. 6A and 6B, multimode fiber 12 is replaced by tubing 54 which, together with single mode fiber 28 and diaphragm 20, define Fabry-Perot cavity 56.

As an alternative to gold nanorods, other nanoparticles, including silver, aluminum, and gold-coated carbon tubes or gold nanoparticles can be employed. Gold nanoparticles can be formed by a suitable method, such as a sodium citrate reduction method, as is known in the art. Examples of suitable methods are described in Enüstün, B. V. and J. Turkevich, *Coagulation of Colloidal Gold,* Journal of the American Chemical Society, 1963. 85(21): p. 3317-3328, and Vakarelski, I. U., Maenosono, R., Kwek, J. W., and Higashitani, K., *Thermal modification of layer-by-layer assembled gold nanoparticle films,* Colloids and Surfaces A: Physicochemical and Engineering Aspects, 340 (1-3), 193-198 (2009) the teachings of which are included herein by reference in their entirety. Following fabrication of the nanoparticles, the energy absorption layer can be formed by depositing the nanoparticles by a layer-by-layer technique, as is known in the art, and as described, for example, in Vakarelski, I. U., Maenosono, R., Kwek, J. W., and Higashitani, K., "Thermal modification of layer-by-layer assembled gold nanoparticle films," Colloids and Surfaces A: Physicochemical and Engineering Aspects, 340 (1-3), 193-198 (2009) the teachings of which are incorporated herein by reference in their entirety. The energy absorption layer can include, for example, between about 1 and about 1,000 bilayers of gold particles. In one embodiment, the energy absorption layer has a thickness in a range of between about 20 micrometers and about 40 micrometers.

Figure 7:
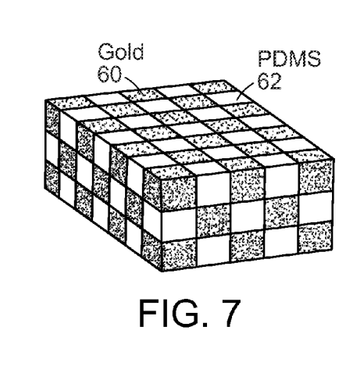
FIG. 7 is a perspective view of one embodiment of an energy absorbing layer of one embodiment of photoacoustic probe of the invention.

Alternatively, the energy absorption film can be fabricated by a nano-imprint technique, wherein a checkerboard-like nanostructure is fabricated to enhance photoacoustic generation efficiency, as shown in FIG. 7. In one embodiment of the nano-imprint technique, a nanostructure includes a combination of gold cells 60 and polymer cells 62, such as polymer cells of polydimethylsiloxane (PDMS). In one embodiment of this method, a PDMS layer is freshly deposited on a surface of a multimodal fiber. A mold is employed to fabricate a pattern of gold cells on a surface. The gold layer is then deposited on top of the PDMS layer. The deposition of gold and PDMS is performed alternately. The dimension of the gold cells can be controlled to a range of between about 10 nanometers and about 100 nanometers. Because different sizes of gold cells correspond to different maximum absorption wavelengths, a phased array technique, such as is known in the art, can be employed. One aspect of the invention includes exciting different wavelengths of laser onto different dimensions of gold cells.

In another embodiment, the same gold nanostructure shown in FIG. 7 can be fabricated by an FIB technique, wherein the sequence of the deposition of gold and PDMS is reversed. Generally speaking, the gold layer is deposited on a surface of the multimodal fiber first, and FIB is introduced to generate a pattern. Thereafter, a PDMS layer is coated on the gold pattern. On the PDMS layer the FIB is introduced again to fabricate the PDMS pattern. The FIB etching and the deposition are performed alternately. The dimensions of the gold cell and the PDMS cell can be controlled very precisely by the FIB.

In still another embodiment, an energy absorbing layer can be formed by exciting a glass with a femtosecond laser to thereby result in a nanospike having a diameter of about 20 nm. After the glass is excited with the femtosecond laser, the whole glass substrate is coated with a gold layer of about 20 nm in thickness. The consequent gold nanostructure can be employed to generate an acoustic wave by application of the photoacoustic principle, as embodied by the invention. Examples of suitable structures are described in "Surface-enhanced Raman scattering on optical material fabricated by femtosecond laser," Wenhui Wang, Haibin Huo, Nan Wu, Mengyan Shen, Charles Guthy, and Xingwei Wang, Proc. SPIE 7673, 76730K (2010), DOI:10.1117/12.852617 and "Surface Enhanced Raman Scattering Sensing with Nanostructures Fabricated by Soft Nanolithography," Haibin Huo, Cong Wang, Haizhou Ren, Michael Johnson, Mengyan Shen Journal of Macromolecular Science, Part A Vol. 46, Issue. 12, 2009, the teachings of both of which are incorporated herein by reference in their entirety. Alternatively, the energy absorption layer can be formed by depositing a thin layer of tin on a glass surface, which is then anodized. A gold layer is then deposited on the resulting porous structure to form another embodiment of the energy absorbing layer.

Figure 8A:
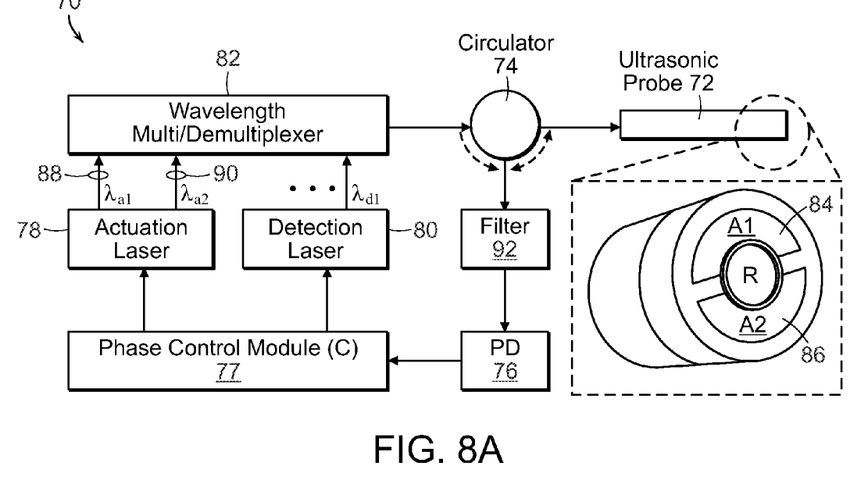
FIGS. 8A through 8C are schematic views of one embodiment of a system of the invention (FIG. 8A) and of ultrasound waves focused on a target (FIG. 8B) and steered in a different direction (FIG. 8C).
Figure 8B:
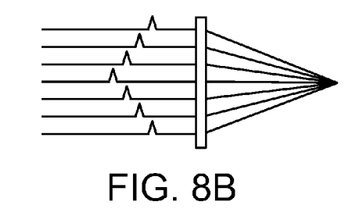
Figure 8C:
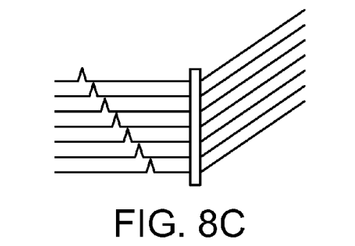

In yet another embodiment, energy absorption layer includes a nanocomposite of a polymer mixed with gold nanoparticles. The gold nanoparticles can be formed either before mixing with the polymer or after mixing gold with the polymer. In one embodiment the polymer is PDMS, which features a relatively high co-efficient of thermal expansion and thus absorb laser light at a corresponding maximum absorption wavelength. In one embodiment of a system for generating ultrasonic waves, an interfering pattern can be directed toward a remote target. As shown in FIG. 8A, system 70 includes photoacoustic probe 72 linked to circulator 74, which is employed to isolate the reflection laser from the input laser. System 70 also includes filter, photodetector (PD) 76, phase control module 77, actuation laser 78, detection laser 80, and wavelength multiplexer 82. In one embodiment, the activity laser and the detecting laser are multiplexed, such as by a time division multiplexing (TDM) scheme. Photoacoustic probe 72 includes distinct energy absorption films 84, 86. In use, phased array and wavelength division multiplexing schemes are employed to steer the direction of the ultrasound generated at energy absorption films 84, 86. The optical absorption peaks of energy absorption films 84, 86 specifically correspond to optical wavelengths from actuation lasers wavelengths 88, 90. Energy absorption films 84, 86 can be independently triggered by lasers with specific wavelengths. The time delay between each trigger and the spatial arrangement of energy absorption films 84, 86 can be employed to form predictable interference patterns, which can be steered in any desired direction, such as is shown in FIGS. 8B and 8C. The signal angle of the interference pattern can be much narrower then that generated from a single source. The ultrasound frequency generated by energy absorption films 84, 86 can be optimized by using adjunctive gain, depth, and focal length controls. Amplitude and phase distributions are capable of producing desired multiple focus field patterns to provide precise control over the intensity and power level of each control point, as well as to provide a weighted solution to increase the excitation efficiency that will enhance the total power delivery of the probe.

Multimode fiber 12 of photoacoustic transducer is connected at core 32 of single mode fiber 28 to a light source 82, light source 82 provides at least two lasers. One laser is pulsed and has a pulse width in a range of between about 1 nanosecond and about several hundred nanoseconds. In one embodiment, the wavelengths of the activating lasers are in a range of between about 500 nm and about 1200 nm. In a specific embodiment, one of the activating lasers has a wavelength of about 527 nm and another activating laser has a wavelength of about 1067 nm. The first pulsed laser is tuned at a maximum absorption wave length of energy absorption film 84, to provide an acoustic signal at energy absorption film 84 that is reflected off a remote object and back to diaphragm R, the consequence deflection of which is detected by changes in the second laser provided by source 82. The second detection laser is tuned in C-band in order to interrogate deflection of diaphragm R, preferably at the lowest possible loss of transmission signal. Optimally, a second pulsed laser with a different wavelength can be employed to provide an acoustic signal at energy absorption film 86. The pulsed lasers do not interfere with each other because their wavelengths are different. The energy absorption films of one embodiment of the invention have different optical absorption peaks that correspond to different optical wavelengths of the activating lasers. In an embodiment of the invention, the energy absorption films are arranged in an array at the optical fiber and the activating lasers independently excite corresponding energy absorption films to form an acoustic wave interference pattern and thereby direct the generated acoustic wave.

In one embodiment, two lasers are employed, namely a 527 nm Nd:YLF nanosecond laser [Quantronix Falcon 527-30-M] and a 1064 nanometer Nd:YVO nano second laser [Quantronix Lsprey-1064-20-L] can be employed for acoustic generation and a tunable diode laser (new focus TLB-6600) with a wavelength range between 1520 and 1570 nanometers for detection can be employed. Alternatively, the wavelength range can be from about 1260 nm to about 1360 nm. A deflection of the diaphragm caused by an ultrasound echo can be calculated by monitoring the Fabry-Perot interference spectrum. In addition, by tuning the wavelength of the detection laser 80 to the quadrature point, which is a point in the reflection interference pattern. The quadrature point is used to help fix the wavelength of the laser so that the interference pattern shift caused by the pressure can be converted into the intensity change. A deflection of the reception element can be obtained by the amplified photo detector. Filter 92 can be used in front of the photo detector to unsure that only the echo signal from the receiver, not the light from the generation lasers, is detected.

Figure 9:
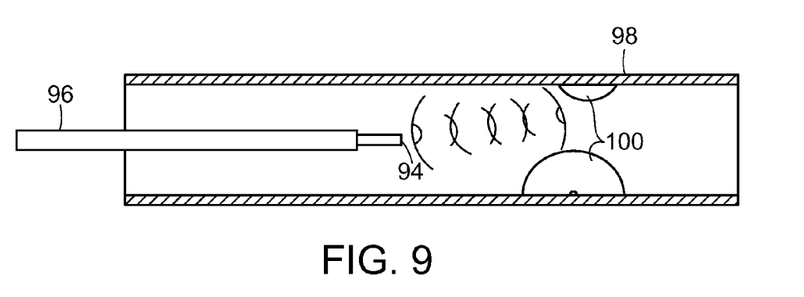
FIG. 9 is a schematic representation of a photoacoustic probe of the invention in a blood vessel of a mammal.

In one embodiment, a photoacoustic probe 94 of the invention can be inserted through catheter 96 into blood vessel 98 of a mammal, and the ultrasonic wavelength of the energy absorption layer can be directed toward a wall of the blood vessel where ultrasonic reflecting of a stenosed area 100 can be detected by the photoacoustic probe, as shown in FIG. 9.

An example of one embodiment of the invention follows.

EXEMPLIFICATION

Introduction

The motivation of the work was to develop a fiber optic ultrasound transducer which generates ultrasound through optical approach (photoacoustic generation). However, a major drawback of photoacoustic generation is low generation efficiency. In order to enhance the efficiency, novel photoacoustic generation materials were developed featuring a high optical energy absorption capability and a high coefficient of thermal expansion (CTE). Such material would be improved in both factors in order to enhance the photoacoustic generation efficiency.

For high optical energy absorption capability, we used gold nanoparticles (Au NPs) because they exhibit high optical radiation energy absorption capabilities at their plasmon resonance frequencies. For high CTE, we used PDMS. We synthesized Au NPs within PDMS directly so that the high optical energy absorption capability and high CTE can be combined together. We called this material the gold nanocomposite. We also tried graphite mixing within PDMS but the generation efficiency was not as high as the one from the gold nanocomposite.

After the gold nanocomposite was synthesized, the material was coated on the tip of an optical fiber for the photoacoustic generation.

Method and Materials

In one specific embodiment, a gold nanocomposite was formed by preparing polydimethylsiloxane (PDMS) by mixing a suitable base and a suitable curing agent, such as are known in the art, in a 10:3 weight ratio. About 30 mg of $HAuCl_4$ salt was finely crushed by a glass rod. About 0.8 grams of the PDMS were mixed with the 30 mg of gold salt. The PDMS mixture was placed in an ultrasonic bath of ice water for about thirty minutes. The PDMS mixture was degassed for about thirty minutes and then coated on a glass slide. The glass slide was coated with the PDMS mixture and baked for about four hours at 70° C.

Experimental Setup

Figure 10:
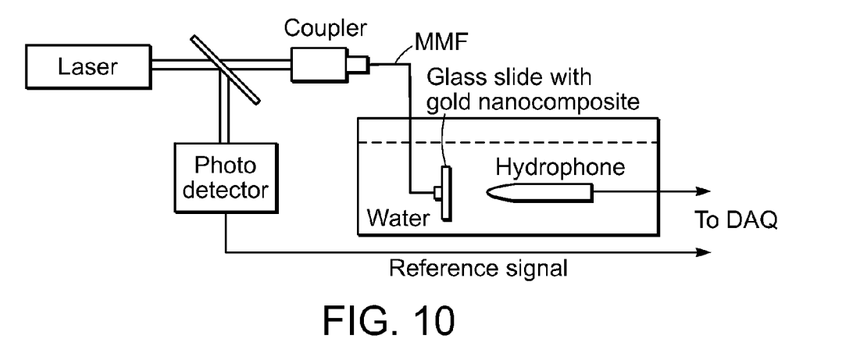
FIG. 10 is a schematic representation of an apparatus employed to demonstrate one embodiment of the invention.

PA generation verification experiments were performed in order to evaluate the efficiency of the PA signal emanating from the gold nanocomposite and the graphite/PDMS mixture. The schematic diagram of the experimental setup is shown in FIG. 10, where the medium in which the experiments were performed was water. A 527 nm Nd:YLF nanosecond laser (Falcon 527-30-M, Quantronix) with a pulse width of 150 ns and a repetition rate of 1 kHz was used as the optical radiation source. The laser beam was split into two beams by a beam splitter. One of the beams was input into a photodetecter (PDA10CS, Thorlabs) as a reference signal and the other beam was coupled into a multi-mode fiber (MMF) (M40L02, Thorlabs) with a core diameter of 400 μm through a coupler (F810SMA-543, Thorlabs). The laser pulse was excited on the glass slide coated with the gold nanocomposite or graphite/PDMS mixture through the optical fiber. A hydrophone (HGL-0200, Onda) was applied to collect the acoustic signals. The reference signals and the acoustic signals were transmitted to a data acquisition system (DAQ) (M2i.4032, Spectrum) with a sampling rate of 50 MHz.

Results from Gold Nanocomposite

Figure 11:
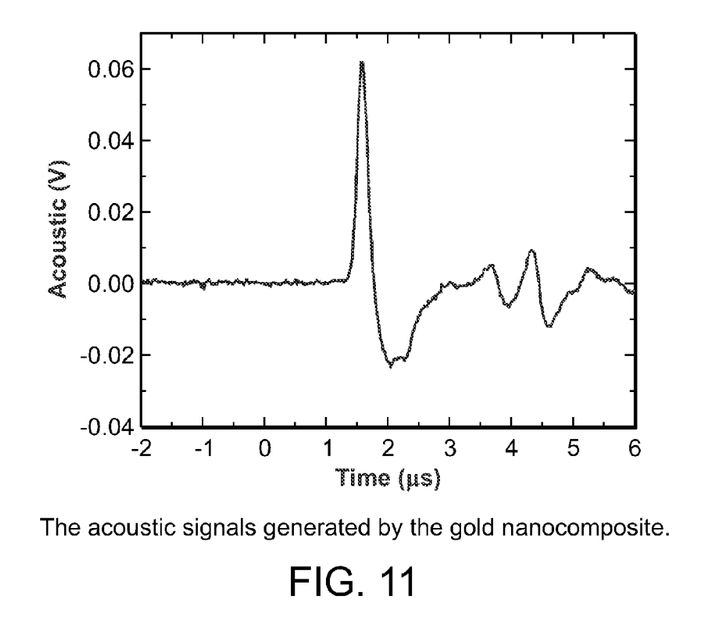
FIG. 11 is a plot of acoustic signals generated by a gold nanocomposite employed by the apparatus represented in FIG. 10.

The optimal generated ultrasound results by the gold nanocomposite are illustrated in FIG. 11. The distance between the hydrophone and the sample was 1.8 mm. The peak to peak amplitude of the acoustic signal can be calculated as 189.49 kPa under the energy density of 13 $mJ/cm^2$. The oscillations behind the peak were caused by the reflections between the hydrophone and the gold nanocomposite film.

Results from Graphite within PDMS

Figure 12:
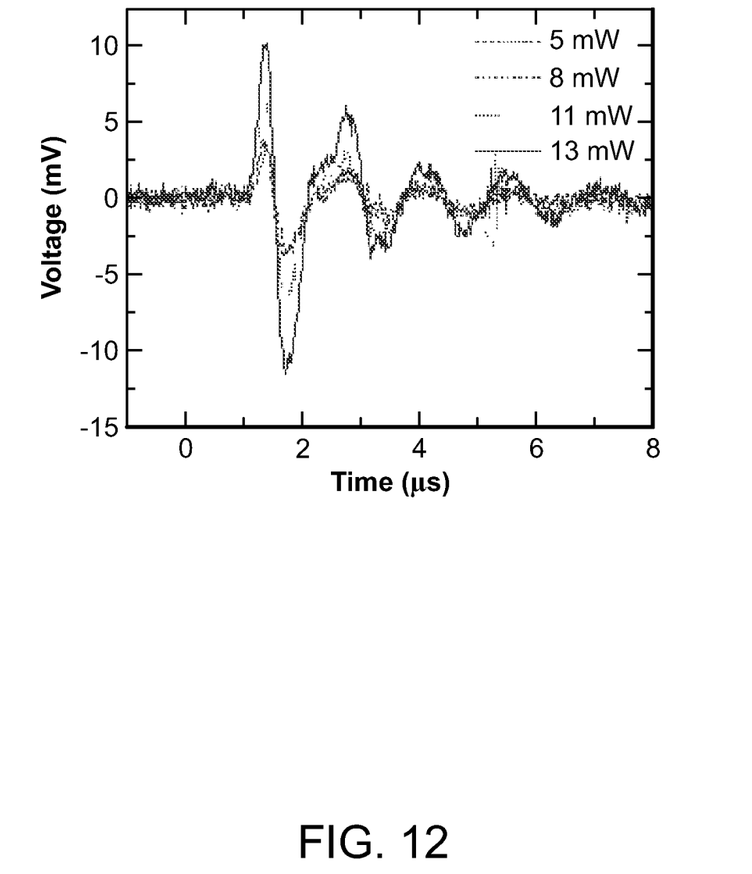
FIG. 12 are plots of acoustic signals generated by the apparatus of FIG. 10.

Acoustic signals generated from the graphite/PDMS is shown in FIG. 12. The laser energy density was 0.86 $mJ/cm^2$. The distance between the hydrophone and the sample was 2.26 mm. The peak to peak amplitude of the acoustic signal can be calculated as 48.89 kPa.

Conclusion

Acoustic signals generated by the gold nanocomposite and the graphite/PDMS were obtained.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A photoacoustic probe, comprising
   a) an optical fiber that defines a recess;
   b) a diaphragm at the optical fiber, the diaphragm defining a surface, whereby at least a portion of the recess and at least a portion of the surface of the diaphragm define a cavity; and
   c) an energy absorption film at the optical fiber,
      whereby an activating laser directed through the optical fiber can excite the energy absorption film to thereby generate an acoustic wave that, upon reflection from a remote surface, can deflect the diaphragm and modify reflection of a detecting laser also directed through the optical fiber.

2. The photoacoustic probe of claim 1, wherein the optical fiber defines a first planar surface.

3. The photoacoustic probe of claim 2, wherein the energy absorption film is at the first planar surface.

4. The photoacoustic probe of claim 3, wherein the diaphragm is within the recess.

5. The photoacoustic probe of claim 4, wherein the diaphragm is recessed within the recess from the first surface.

6. The photoacoustic probe of claim 2, wherein the optical fiber includes a second surface that is raised from the first surface and is essentially parallel to the first surface.

7. The photoacoustic probe of claim 6, wherein the recess is further defined by an edge of the second surface and the diaphragm is at the second surface.

8. The photoacoustic probe of claim 7, wherein the energy absorbing film is peripheral to the raised second surface when viewed orthogonally to the plane of the second surface.

9. The photoacoustic probe of claim 2, wherein the diaphragm is at the first planar surface.

10. The photoacoustic probe of claim 9, wherein the energy absorption film is at the diaphragm.

11. The photoacoustic probe of claim 10, wherein the energy absorption film is peripheral to the portion of the diaphragm that, in combination with the optical fiber, defines the cavity.

12. The photoacoustic probe of claim 11, wherein the optical fiber and the diaphragm together define a trench that at least partially partitions the energy absorption film from the portion of the diaphragm that, in combination with the optical fiber, defines the cavity.

13. The photoacoustic probe of claim 1, wherein the probe includes a plurality of energy absorption films.

14. The photoacoustic probe of claim 13, wherein at least a portion of the energy absorption films are in the same plane.

15. The photoacoustic probe of claim 14, wherein the energy absorption films are at least partially partitioned by a trench defined at least in part by the optical fiber.

16. The photoacoustic probe of claim 15, wherein the trench is further defined by the diaphragm.

17. The photoacoustic probe of claim 1, wherein the energy absorption film includes gold.

18. The photoacoustic probe of claim 17, wherein the energy absorption film further includes at least one of silver, polydimethylsiloxane (PDMS), anodized aluminum oxide (AAO), anodized tin oxide (ATO), and epoxy.

19. The photoacoustic probe of claim 17, wherein at least a portion of the gold is in the form of at least one of nanoparticles, nanostructures and nanocomposites.

20. The photoacoustic probe of claim 19, wherein the nanoparticles are in the form of nanorods.

21. The photoacoustic probe of claim 20, wherein the nanorods have an aspect ratio in a range of from about 1.0 to about 6.5 and an effective radius in a range of from about 8 nm to about 25 nm.

22. The photoacoustic probe of claim 21, wherein at least a portion of the gold is in the form of nanoparticles.

23. The photoacoustic probe of claim 22, wherein the nanoparticles are in the form of nanospheres.

24. The photoacoustic probe of claim 23, wherein the nanospheres have an average diameter in a range of from about 10 nm to about 100 nm.

25. The photoacoustic probe of claim 22, wherein the nanoparticles are in the form of nanoshells.

26. The photoacoustic probe of claim 25, wherein the nanoshells have a total radius in the range from about 50 nm to about 150 nm and a core/shell ratio in a range of from about 0.1 to about 1.

27. The photoacoustic probe of claim 1, wherein the optical fiber is a multimode optical fiber and the probe further includes a single-mode fiber connected to the multimode optical fiber.

28. The photoacoustic probe of claim 1, further including tubing at the optical fiber, and whereby the tubing, the optical fiber and the diaphragm define the cavity.

29. A method of detecting an acoustic wave, comprising the steps of:
   a) directing an activating laser through an optical fiber to an energy absorption film at the optical fiber to thereby generate an acoustic wave;
   b) directing a detecting laser through the optical fiber and a cavity to a diaphragm at the optical fiber, the cavity being defined by the optical fiber and the diaphragm; and
   c) measuring an interference pattern generated at least in part by a reflection of the detecting laser from a surface of the diaphragm,
      wherein the interference pattern is indicative of the reflection of the acoustic wave from a remote surface.

30. The method of claim 29, further including the step of inserting the optical fiber into a chamber or lumen.

31. The method of claim 30, wherein the chamber or lumen is inside of a mammalian body.

32. The method of claim 31, wherein the detecting laser includes a tunable diode laser.

33. The method of claim 29, wherein the activating laser is actuated separately in time from measurement of the interference pattern generated by the detecting laser.

34. The method of claim 29, further comprising the step of multiplexing the activating laser and the detecting laser.

35. The method of claim 34, wherein the multiplexing occurs according to a time division multiplexing (TDM) scheme.

36. The method of claim 29, wherein the activating laser includes at least two activating lasers of different wavelengths and wherein the energy absorption layer includes at least two energy absorption films, each activating laser activating a different energy absorption film at the optical fiber.

37. The method of claim 36, wherein the wavelengths of the activating lasers are in a range of from about 500 nm to about 1200 nm.

38. The method of claim 37, wherein the wavelength of one of the activating lasers is 527 nm and the wavelength of a second activating laser is 1064 nm.

39. The method of claim 36, wherein the activating lasers are pulsed lasers.

40. The method of claim 36, wherein the energy absorption films have different optical absorption peaks that correspond to the different optical wavelengths of the activating lasers.

41. The method of claim 40, wherein the energy absorption films are arranged in an array at the optical fiber and the activating lasers independently excite corresponding energy absorption films to form an acoustic wave interference pattern and thereby direct the generated acoustic wave.

42. A photoacoustic probe system, comprising
a) a photoacoustic probe, including
  i) an optical fiber that defines a recess,
  ii) a diaphragm at the optical fiber, the diaphragm defining a surface, whereby at least a portion of the recess and at least a portion of the diaphragm define a cavity, and
  iii) an energy absorption film at the optical fiber, whereby an activating laser directed through the optical fiber can excite the energy absorption film to thereby generate an acoustic wave that, upon reflection from a remote surface, can deflect the diaphragm and modify reflection of a detecting laser also directed through the optical fiber;
b) a circulator linked to the photoacoustic probe;
c) a wavelength multi/demultiplexer linked to the inductor;
d) an activation laser linked to the wavelength multi/demultiplexer;
e) a detection laser linked to the wavelength multi/demultiplexer;
f) a phase control module coupled to the actuation laser and the detection laser;
g) a filter linked to the circulator; and
h) a photodetector linked to the filter and the phase control module.

\* \* \* \* \*